(12) United States Patent
Haendler

(10) Patent No.: US 6,518,041 B1
(45) Date of Patent: Feb. 11, 2003

(54) HORMONE RESPONSE ELEMENT THAT BINDS AN ANDROGEN AND PROGESTERONE RECEPTOR

(75) Inventor: Bernhard Haendler, Berlin (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/447,349

(22) Filed: Nov. 22, 1999

(30) Foreign Application Priority Data

Nov. 20, 1998 (DE) .......................................... 198 55 013

(51) Int. Cl.$^7$ ........................... C12P 21/06; C12N 1/20; C12N 15/74; C12N 5/00; C07H 21/04
(52) U.S. Cl. ................... 435/69.1; 435/252.3; 435/325; 435/471; 536/23.5
(58) Field of Search ........................ 536/23.5; 435/471, 435/69.1, 325, 252.3

(56) References Cited

U.S. PATENT DOCUMENTS 5,597,693 A    1/1997   Evans et al.

FOREIGN PATENT DOCUMENTS

| EP | 0798378 | 10/1997 | |
|----|---------|---------|---|
| WO | WO 89/05355 | 6/1989 | |
| WO | WO 90/11273 | 10/1990 | |
| WO | WO 90/14356 | 11/1990 | |
| WO | WO 91/06677 | 5/1991 | |
| WO | WO 92/18522 | 10/1992 | |
| WO | WO 94/01548 | * 1/1994 | |
| WO | WO 94/28150 | 12/1994 | |
| WO | WO 96/24357 | 8/1996 | |
| WO | WO 96/33724 | 10/1996 | |
| WO | WO 96/34091 | 10/1996 | |
| WO | WO 96/36230 | 11/1996 | |
| WO | WO 98/48825 | 11/1998 | |
| WO | WO 98/49555 | 11/1998 | |

OTHER PUBLICATIONS

Bonaldo M, et al. Genome Res. 6:791–806, 1996.*
Sutton K.A. Accession No. U50747 Apr. 4, 1996.*
U. Schwidetzky et al., *Biochem. J.*, vol. 321, pp. 325–332 (1997).
A.R. Clark et al., *Biochem. J.*, vol. 309, pp. 863–870 (1995).
S. Maiti et al., *J. of Biol. Chemistry*, vol. 271(29):17536–17546 (1996).
S. Maiti et. al., *Chemical Abstracts*, Abs. No. 134295, vol. 125, No. 11 (1996).

* cited by examiner

*Primary Examiner*—Gary Kunz
*Assistant Examiner*—Robert S. Landsman
(74) *Attorney, Agent, or Firm*—Millen, White, Zelano & Branigan, P.C.

(57) ABSTRACT

The invention relates to a novel HRE (hormone response element) which binds to an androgen or progesterone regulated receptor.

29 Claims, 7 Drawing Sheets

HORMONE RESPONSE ELEMENT THAT BINDS AN ANDROGEN AND PROGESTERONE RECEPTOR

The invention relates to a new HRE (hormone response element, hormone receptor binding site), which is bonded by an androgen and progesterone receptor, its sequence and its use.

Steroid receptors are transcription factors that have a ligand binding site, a DNA binding site and several trans-activation functions. If the ligand binds the steroid, the conformation of the receptor changes. By this change in conformation, the receptor can form a dimer and bind to a specific, two-stranded DNA sequence, the so-called HRE (hormone response element, hormone receptor binding site) and interact with coactivators and other transcription factors. As a consequence, the transcription of the target gene, thus the gene that is regulated by the HRE, is activated. These HREs are usually components of promoter regions of such target genes, but they can also be found in the intron areas or in the 3'-part of the gene. For the HRE of the androgen receptor, a consensus sequence (SEQ ID NO: 4) GG(T/A)ACAnnnTGTTCT has been found (Roche et al. 1992, Mol. Endocrinol. 6, 2229–2235). In this case, n refers to any nucleotide. The half-elements, which are the defined nucleotides before or after the "nnn" sequence, are approximately palindromic. It was shown that the sequence (SEQ ID NO: 5) GGTACAtctTGTTCA, which occurs in the promoter of the highly androgen-regulated CRISP-i-gene, has a high binding affinity to the androgen receptor (Schwidetzky et al. 1997, Biochem. J. 321, 325–332). This sequence is referred to in the following consensus-HRE. It is detected, however, not only by the androgen receptor but also by the glucocorticoid and progesterone receptor. The HRE, however, binds the promoter region of the probasin gene selectively to the androgen receptor and not to the glucocorticoid receptor (F. Claessens et al. 1996, J. Biol. Chem. 271, 19013–19016). No information on the binding of the progesterone receptor is present here. By an in vitro selection method, a new DNA sequence named IDR17, which can bind the androgen receptor, was recently found (Zhou et al. 1997, J. Biol. Chem. 272, 8227–8235). Various tests showed that this sequence has a high selectivity for the androgen receptor in comparison to the glucocorticoid receptor. A comparison with the progesterone receptor was not described. The sequence IDR17 is a sequence that was found in vitro; there is no indication as to whether it also occurs in vivo and has a function there as an HRE.

The knowledge on HREs is helpful in the development of medications for the treatment of hormone-dependent diseases. In the treatment of prostate cancer with antiandrogens, which inhibit the binding of the androgen receptor to the consensus HRE, it is frequently shown that not all androgen-regulated genes are adjusted downward and/or the antiandrogens are no longer active after a certain treatment time. These findings thereupon point to the fact that different HREs must be provided that regulate various genes and are responsible for the hormone-dependency. For successful hormone therapy, it is therefore desirable to know other HREs to which the androgen receptor binds. Specifically active natural hormones, synthetic hormones or antihormones could then be identified. The latter can then turn on or off the genes that are relevant for the diseases. To date, only a few genes that are regulated by androgens and their HREs are known. Examples of this are the probasin gene and the C3(1) gene, which are both induced in rat prostates by androgen (F. Claessens et al. 1989, Biochem. Biophys. Res. Commun. 164, 833–840; P. S. Rennie et al. 1993, Mol. Endocrinol. 7, 23–36). In the rat epididymis, the pem gene is expressed in an androgen-dependent manner (S. Malti et al. 1996, J. Biol. Chem. 271, 17536–17546). The approximate position of two initial transcription sites is described, but the HRE is not known.

It is desirable to have available a new HRE for the androgen receptor. The invention provides a new HRE, which binds the androgen and progesterone receptor and which contains a. a DNA sequence of the general formula (SEQ ID NO: 6) $(N)_x$TCTCATTCTGTTCC, whereby N, independently of one another and in any combination, is A, T, C or G, and x is equal to 0–3, b. a variation of the sequence that is mentioned under a., or c. a DNA sequence, which is complementary to the DNA sequence that is mentioned under a. or b.

A variation of the sequence can be, e.g., an allelic variation. An allelic variation is defined as a mutation, i.e., a change in the DNA sequence, which is characterized by natural deletion, addition or substitution of nucleotides. Any of these changes can occur alone or in combination with other changes, once or several times in the DNA sequence. The binding properties of the HRE are changed only insignificantly by these changes. Allelic variants are to have an at least 80%, preferably an 85% or most preferably 90% sequence identity in the sequence that is mentioned under a. The DNS sequence according to the invention is present in vivo as a double strand, i.e., it binds to the DNA sequence that is complementary to it.

In addition, a variation can be a sequence that hybridizes with the sequence according to the invention under stringent conditions. For an HRE with 17 nucleotides, stringent conditions are a hybridization temperature of 35° C., preferably 38° C., most preferably 41° C. in a QuickHyb buffer (stratagenes).

Hybridization conditions can be chosen to select nucleic acids which have a desired amount of nucleotide complementarity with the naturally-occurring nucleotide sequences. A nucleic acid capable of hybridizing to such sequence, preferably, possesses, e.g., about 85%, more preferably, 90%, 92%, and even more preferably, 95%, 97%, or 100% complementarity, between the sequences. The present invention particularly relates to nucleic acid sequence variations which hybridize to the nucleotide sequence set forth in SEQ ID NOS. 1–3 under low or high stringency conditions.

Nucleic acids which hybridize to the mentioned sequences can be selected in various ways. For instance, blots (i.e., matrices containing nucleic acid), chip arrays, and other matrices comprising nucleic acids of interest, can be incubated in a prehybridization solution (6×SSC, 0.5% SDS, 100 µg/ml denatured salmon sperm DNA, 5×Denhardt's solution, and 50% formamide), at 30° C., overnight, and then hybridized with a detectable oligonucleotides probe, (see below) in a hybridization solution (e.g., 6×SSC, 0.5% SDS, 100 µg/ml denatured salmon sperm DNA and 50% formamide), at 42° C., overnight in accordance with known procedures. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity. Other non-limiting examples of high stringency conditions includes a final wash at 65° C. in aqueous buffer containing 30 mM NaCl and 0.5% SDS. Another example of high stringent conditions is hybridization in 7% SDS, 0.5 M NaPO4, pH 7, 1 mM EDTA at 50° C., e.g., overnight, followed by one or more washes with a 1% SDS solution at 42° C.

Whereas high stringency washes can allow for less than 5% mismatch, relaxed or low stringency wash conditions (e.g., wash twice in 0.2% SSC and 0.5% SDS for 30 min at 37° C.) can permit up to 20% mismatch. Another non-limiting example of low stringency conditions includes a final wash at 42° C. in a buffer containing 30 mM NaCl and 0.5% SDS. Washing and hybridization can also be performed as described in Sambrook et al., Molecular Cloning, 1989, Chapter 9.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm= (number of A's and T's)×2° C.+(number of C's and G's)×4° C. For longer molecules, Tm=81.5+16.6log 10 [Na+]+0.41 (%GC)−600/N where [Na+] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

The androgen and progesterone receptor, however, not the gluococorticoid receptor, specifically binds to the HRE according to the invention. The HRE according to the invention reacts in a very much more sensitive manner to the androgen and progesterone receptor than the consensus-HRE and the IDR17-HRE, which results in a stronger induction of the target gene (see Example 4). Cotransfection with expression constructs, which code for proteins, from which it is to be assumed that they interact with the androgen receptor, result in a stronger stimulation of the HRE according to the invention (ARE17) in comparison to the consensus-HRE (see Example 4). The androgen stimulation of the HRE according to the invention can be inhibited simply by 125 ng/ml of geldanamycin unlike the consensus-HRE, which is thus more likely stimulated and is inhibited only at a higher concentration of geldanamycin (see Example 4). Geldanamycin is a substance that inhibits the action of steroid receptors (D. F. Smith et al. 1995, Cell. Biol. 15, 6804–6812). HREs, which are bonded by the estrogen, glucocorticoid or mineralocorticoid receptor, consist of 2 almost palindromic half-elements (Evans et al. U.S. Pat. No. 5,597,693). The consensus-HRE for the androgen receptor also has an almost palindromic structure. The HRE according to the invention, however, does not have any palindromic structure and can more likely be viewed as a "direct repeat" of the half-element TGTTCT. This structural difference and the above-mentioned differences indicate that the interaction between the androgen receptor and the HRE according to the invention is unlike that between the androgen receptor and the consensus-HRE. It should therefore be possible to modify the interaction with the HRE according to the invention by another mechanism and by other androgens or antiandrogens than the interaction with the consensus-HRE.

Preferred is an HRE according to the invention, in which x=0, and the DNA sequence corresponds to Seq. ID No. 3. In addition, an HRE according to the invention in which x=3 is preferred. Most preferred is an HRE according to the invention, in which x=3 and N=AGA and the DNA sequence corresponds to Seq. ID No. 1.

The HRE-DNA sequence according to the invention can be used for the detection of genes that are regulated by androgen and/or progesterone. This can be done in human or animal tissue. As a result, new genes can be identified, or the androgen and/or progesterone regulation of known genes and unknown genes can be detected. The detection can be carried out by, e.g., computer-supported analysis of DNA data banks, DNA sequencing or by a point mutation screening process (e.g., sequencing of PCR-amplified genome fragments or single strand conformation polymorphism SSCP) (A. C. Goodeve 1998, Clin. Lab. Hematol. 20, 3–19). Data analysis can be carried out using conventional algorithms, such as BLAST. In this case, the DNA sequence that is analyzed in each case is compared to the HRE-DNA sequence according to the invention. In addition, an oligonucleotide can be synthesized with the HRE sequence according to the invention. In this case, the synthesis is carried out according to routine methods as they are described in, e.g., M. H. Caruthers et al. 1983, Gene Amplif. Anal. 3, 1–26. The oligonucleotide can be radiolabeled or can contain a detectable radical, such as, e.g., digoxigenin, alkaline phosphatase, biotin, fluorescein, rhodamines, Texas RED, Oregon Green or BODIPY dyes. With the aid of this oligonucleotide that corresponds to the HRE-DNA sequence according to the invention, the genes, which are regulated by the HRE according to the invention, can be detected by screening of genomic banks, a Southern Blot or in situ hybridization or by other methods that are known to one skilled in the art. Useful oligonucleotides comprise, e.g., 6–25 nucleotides, preferably, 8–17 nucleotides.

An HRE sequence according to the invention or a sequence that is regulated by an HRE sequence according to the invention can be used for detection of an alteration in the expression of androgen and/or progesterone-regulated genes. Thus, e.g., diseased cells can be compared to normal cells. A sequence that is regulated by an HRE sequence according to the invention can be, e.g., a sequence from the coding area of a target gene.

In addition, the invention relates to the use of an oligonucleotide corresponding to a DNA sequence according to the invention for detection of mutations in expression-regulation elements, especially HRE's, which are regulated by androgen or progesterone, in human or animal tissue. In this case, these can be normal cells, i.e., unchanged cells, established cell lines and tumor cells. The detection of such mutations can be carried out by, e.g., sequencing of genomic DNA that is isolated from these tissues or cells or by a point mutation screening process (A. C. Goodeve 1998, Clin. Lab. Haematol. 20, 3–19). Such mutations can play a role in the often observed relapse in the treatment of tumor patients with antihormones. The interaction of the androgen or progesterone receptor after antagonists or partial agonists are bonded with the mutated HRE can be changed and as a result lead to an altered expression or repression of genes. The detection of such mutations should allow a therapy to be better adapted to the patient in whom such mutations have been found.

The invention also relates to vectors that comprise an HRE according to the invention in operative linkage with the gene that is to be expressed. In this case, the HRE according to the invention can be present in several copies, preferably in 1–4 copies. As an operative linkage, a minimal promoter sequence can be used. In the literature, a number of vectors and minimal promoters are known that can be used. For example, the vectors pGL3-Basic or pGL3-Enhancer can be used. As a promoter, the TK minimal promoter (G. R. Reyes et al. 1982, J. Gen. Virol. 62, 191–206) or comparable minimal promoters can be used. A minimal promoter is a promoter that has only the TATA box and an initial transcription point. The DNA sequence that is detected by the protein complex TFIID is referred to as a TATA box.

With the vector according to the invention or a DNA that contains an HRE according to the invention, cells can be transformed. These transformed cells are also the subject of this invention. The cells can be eukaryotic cells, thus even, e.g., yeasts. Suitable cells are, e.g., PC-3 cells (M. E. Kaighn et al., 1979, Invest. Urol. 17 16–23), LNCaP cells (J. S. Horoszewicz et al., 1983, Cancer Res. 43 1809–1818), CV-1 cells (F. C. Jensen et al., 1964, Proc. Natl. Acad. Sci. USA 52, 53–59), HeLa cells (T. T. Puck et al., 1956, J. Exp. Med. 103 273–284) and Dunning cells (D. D. Mickey et al., 1977, Cancer Res. 37 4049–4058). The transfection can be performed by usual methods, such as, e.g., with the transfection reagents calcium chloride, Fu genes, lipoTAXI, DOTAP, lipofectin, lipofectamines, superfect, or by elecroporation or with the aid of a gene gun. Methods for transfections are described in Molecular Cloning, A Laboratory Manual (Sambrook et al., 1989, Cold Spring Harbor Laboratory Press).

The cells according to the invention can be used for the expression of the gene that is linked operatively with the HRE sequence. A polypeptide that can be bonded to the HRE element and that has an additional ligand binding domain preferably contains the cell. The androgen receptor or the progesterone receptor is especially preferred as a polypeptide. The cells can be transformed in a stable or transient manner with the androgen receptor gene or the progesterone receptor gene with parts thereof or with parts thereof in combination with transactivation domains of other factors, and the expressions of proteins are indicated by the addition of an androgen or a progestin to the cultivated cells. Parts of the androgen or progesterone receptor can be, e.g., the ligand-binding domains, the transactivation domains and the DNA-binding domains. Transactivation domains of other factors can be, e.g., Gal 4-transactivation domains or VP16-transactivation domains.

The invention also relates to a test system for substances with hormone receptor binding ability that comprise
   a. a DNA sequence according to the invention in operative linkage with a heterologous gene that is to be expressed or transcribed,
   b. a polypeptide that can be bonded with the DNA according to the invention that is described under a.

A gene that is to be expressed can code a detectable protein. A gene that is to be transcribed can be transcribed in a detectable RNA.

In addition, the invention relates to a test system for detection of test substances with androgenic activity, whereby
   a. a reporter gene is expressed in the cells according to the invention and
   b. these cells, if they contain little or no androgen receptors, are transformed in addition with an expression vector for the androgen receptor,
   c. the cells are cultivated in the presence or absence of the test substances, and
   d. the alteration of the expression of the reporter gene is measured.

The invention also relates to a test system for the detection of test substances with antiandrogenic activity, whereby
   a. a reporter gene is expressed in the cells according to the invention and
   b. these cells, if they contain little or no androgen receptors, are transformed in addition with an expression vector for the androgen receptor,
   c. the cells are cultivated in the presence or absence of test substances in the simultaneous presence of an androgen, and
   d. the alteration of the expression of the reporter gene is measured and a test system for the detection of test substances with progestin activity, whereby
   a. a reporter gene is expressed in the cells according to the invention, and
   b. these cells, if they contain little or no progesterone receptor, are transformed in addition with an expression vector for the progesterone receptor,
   c. the cells are cultivated in the presence or absence of test substances, and
   d. the alteration of the expression of the reporter gene is measured.

Finally, the invention provides a test system for the detection of test substances with antiprogestin activity, whereby
   a. a reporter gene is expressed in the cells according to the invention, and
   b. these cells, if they contain little or no progesterone receptor, are transformed in addition with an expression vector for the progesterone receptor,
   c. the cells are cultivated in the presence or absence of the test substances with the simultaneous presence of a progestin, and
   d. the alteration of the expression of the reporter gene is measured.

Reporter genes can be, e.g., luciferase genes, chloroamphenicolacetyl transferase genes, urokinase genes, green fluorescence protein genes and β-galactosidase genes. An androgen can be selected from the group that consists of R1881, testosterone, dihydrotestosterone and testosterone derivatives, and a progestin can be selected from the group that consists of levonorgestrel, progesterone, R5020, drospirinone and dienogest. A substance with antiandrogenic activity prevents the action of the androgen on the androgen receptor, and an anti-progestin inhibits the effect of progesterone or progestins on the progesterone receptor.

Preferred is the use of the luciferase reporter gene and of PC-3 cells that have been transformed in advance in a stable manner with an expression vector for the androgen receptor (PC-3/AR cells) or in a transient parallel manner. In addition, the use of the TK minimal promoter is preferred. If PC-3/AR cells with an expression vector for the androgen receptor and a construct of 2 copies of the HRE according to the invention, the TK minimal promoter and the luciferase gene are transformed, and the androgen R1881 (C. Bonne and J.-P. Raynaud 1975, Steroids 26, 227–232) is added, a 10.5-fold induction of the luciferase activity is measured (see Example 3 and FIG. 4). If PC-3/AR cells with an expression vector for the glucocorticoid receptor and a construct of 2 copies of the HRE according to the invention, the TK minimal promoter and the luciferase gene are transformed, and the glucocorticoid dexamethasone is added, only a 1.9-fold induction is measured. If, instead of 2 copies of the HRE according to the invention, 4 copies in the same system are used, a 46-fold increase of the luciferase activity with R1881 and a 1.8-fold increase with dexamethasone are measured. If PC-3/AR cells with an expression vector for the progesterone receptor and a construct of 4 copies of the HRE according to the invention, the TK minimal promoter and the luciferase gene are transformed, and the progestin levonorgestrel is added, a 52.2-fold induction is measured (see Example 3 and FIG. 5). A progestin is a synthetic progesterone analog. The use of the test systems is not limited to the test substances that are described in the examples, rather, these test systems can be used for screening large substance holdings.

The subject of the invention is also a process for the detection of test substances with use of the test systems according to the invention.

The invention also provides a process for the preparation of pharmaceutically active substances, whereby
  a. the substances that are to be tested are brought into contact with a test system according to the invention,
  b. the action of the substances on the test system in comparison to the controls is measured, and
  c. a substance that shows a modulation of the expression of the heterologous peptide in step b. is identified.

The invention also relates to a process for the preparation of a pharmaceutical agent, whereby
  a. the substances that are to be tested are brought into contact with a test system according to the invention,
  b. the action of the substances on the test system optionally in comparison to the controls is measured,
  c. a substance that shows a modulation of the expression of the heterologous polypeptide in step b. is identified,
  d. and the substance that is identified in step c. is mixed with the formulation substances that are commonly used in pharmaceutics.

The invention also provides a process for the preparation of a pharmaceutical agent, whereby
  a. substances are brought into contact with a test system according to the invention,
  b. the action of the substances on the test system in comparison to the controls is measured,
  c. a substance that shows a modulation of the expression of the heterologous polypeptide in step b. is identified,
  d. the substance that is identified in step c. is optionally optimized, and
  e. this optionally optimized substance is mixed with formulation substances that are commonly used in pharmaceutics.

Preferred are substances that increase or inhibit at least 10-fold the reporter gene activity in the test systems according to the invention. A substance that is identified by a process according to the invention can optionally be optimized relative to metabolic stability, activity in a test system according to the invention and/or bio-availability. In this respect, methods that are standard in chemistry can be used.

The preferred preparations consist of a form for dispensing that is suitable for oral, enteral or parenteral administration. Such forms for dispensing are, for example, tablets, film tablets, coated tablets, pills, capsules, powder or depot forms as well as suppositories. Corresponding tablets can be obtained by, for example, mixing the active ingredient with known adjuvants, for example inert diluents such as dextrose, sugar, sorbitol, mannitol, polyvinylpyrrolidone, explosives such as corn starch or alginic acid, binders such as starch or gelatin, lubricants such as carboxypolymethylene, carboxymethylcellulose, cellulose acetate phthalate or polyvinyl acetate. The tablets can also consist of several layers.

Coated tablets can correspondingly be produced by coating cores that are produced analogously to tablets with agents that are commonly used in coated tablet coating, for example polyvinylpyrrolidone or shellac, gum arabic, talc, titanium oxide or sugar. In this case, the coated tablet shell can also consist of several layers, whereby the adjuvants that are mentioned above in the tablets can be used. Capsules that contain active ingredients can be produced, for example, by the active ingredient being mixed with an inert vehicle such as lactose or sorbitol and encapsulated in gelatin capsules. The substances according to the invention can also be used in suitable solutions such as, for example, physiological common salt solution, as an infusion or injection solution. For parenteral administration, especially oily solutions, such as, for example, solutions in sesame oil, castor oil, and cottonseed oil, are suitable. To increase solubility, solubilizers, such as, for example, benzyl benzoate or benzyl alcohol, can be added. It is also possible to incorporate the substances that are available and are obtained via the process according to the invention in a transdermal system, and thus to administer them transdermally.

With the process according to the invention for the detection of test substances, such substances can also be prepared that mediate a selective binding of a polypeptide, preferably the androgen receptor or the progesterone receptor to the HRE according to the invention compared to the known consensus sequence.

The pharmaceutical agent according to the invention can be used for the production of a medication for the treatment of androgen- or progesterone-dependent diseases. Such diseases can be, e.g., prostate cancer or testicular tumors.

The pharmaceutical agent according to the invention can be used for the production of a medication for birth control. For male birth control, e.g., the expression of genes that are necessary for forming mature sperm can be inhibited.

EXAMPLES

The molecular-biological methods that are used in the examples, such as, e.g., polymerase-chain reaction (PCR), production of cDNA, cloning of DNA, sequencing of DNA, transfection, determination of the luciferase activity, were performed as described in known textbooks, such as in, for example, Molecular Cloning, A Laboratory Manual (Sambrook et al., 1989, Cold Spring Harbor Laboratory Press).

Example 1

Androgen-dependency of the Pem Gene Expression in the Epididymis

By daily treatment with a GnRH antagonist, mice were chemically castrated (B. Haendler et al. 1997, Eur. J. Biochem. 250, 440–446). By castration, the androgen is biosynthesis is suppressed. After 1 or 2 weeks, the epididymis was removed, and RNS was isolated therefrom. The latter was then converted into cDNA and used for PCR, which was performed with the aid of pem-specific oligonucleotide primers. After separation in an agarose gel, the quantities of pem amplification product could be compared. The results showed that the pem expression after castration was very greatly reduced. Only about 1% of the control quantities was measured. This indicates that very strong androgen response elements in the pem gene must be present.

Example 2

Identification of the HRE According to the Invention

An analysis of the published pem-promoter region of the rat shows no sequence that is closely related to the consensus-HRE. There are only shorter areas that are similar to the half-element TGTTCT and of which it is not known whether they represent an HRE. One of these areas, surprisingly enough, showed a very strong androgen induction in the test that is described in Example 3. We named these areas ARE17. Its sequence corresponds to Seq. ID No. 1.

Example 3

Detection of the EIRE According to the Invention in the Mouse Pem-Promoter Region A 310 base-pair-long promoter fragment was amplified from genomic mouse DNA by PCR with the aid of the GenomeWalker kit (Clontech). An antisense primer (SEQ ID NO: 7) 5'-GTTCTTCCGAGTCTTCCTTGAC-3' (specific for the pem gene) and a sense primer (SEQ ID NO: 8) 5'-GTAATACGACTCACTATAGGGC-3' (which detects an adaptor sequence at the end of the genomic DNA-fragments) were used for this. After gel purification, the amplified fragment was cloned in a plasmid and sequenced. The sequence is depicted in Seq. ID No. 2. The translation initiation point is at position 313–315 (ATG). It is 88.5% identical with the pem-promoter region (position 1–312) of the rat. It contains the ARE17 with the sequence that is indicated in Seq. ID No. 1 at the same point (position 228–244) as the promoter region of the rat.

Example 4

Test Systems

Figure 1:
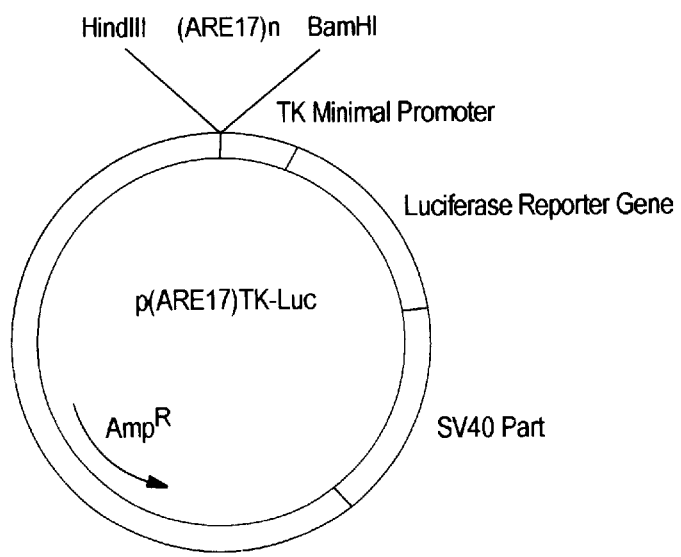
FIG. 1 shows the map of the reporter plasmid, which contains the HRE according to the invention, named ARE17, with the sequence that corresponds to Seq. ID No. 1 as 1–4 copies.
Figure 2:
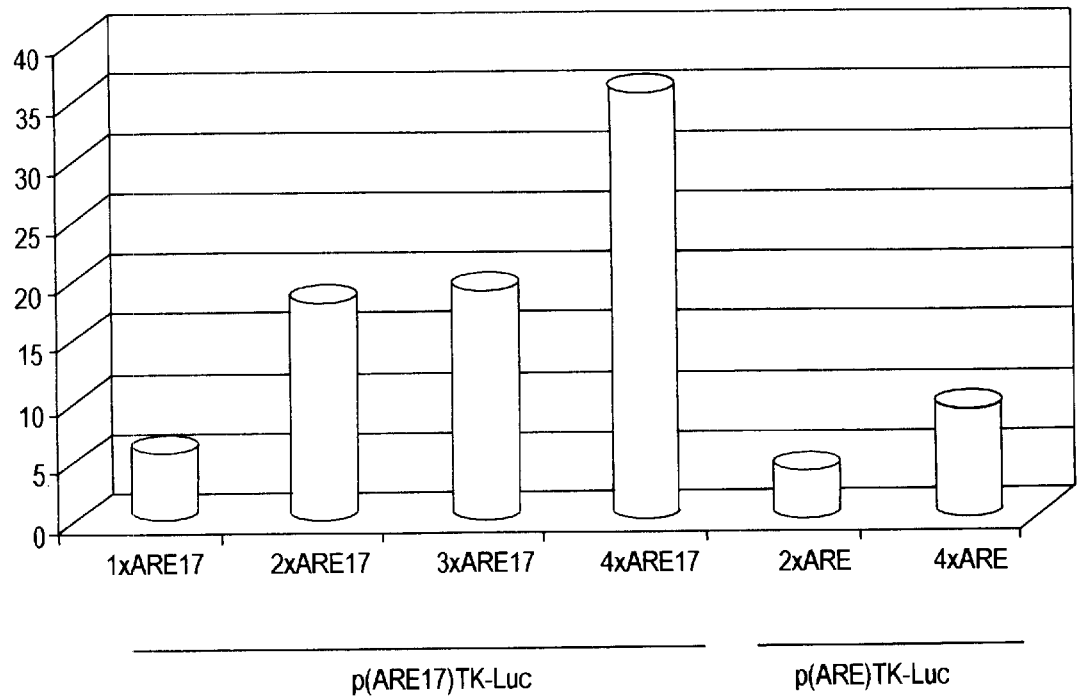
FIG. 2 shows the stimulation of the ARE17 according to the invention by an androgen in comparison to a consensus HRE (named ARE here). The indicated number of copies of the element was introduced in the reporter vector. This was transformed in PC-3/AR cells, and the luciferase activity was measured after R1881 treatment. The y-scale indicates how many times stronger the stimulation was in comparison to cells that were not treated with R1881.

Test systems were compared that contained either an HRE according to the invention that corresponds to Seq. ID No. 1 (ARE17) or the consensus-HRE with the sequence (SEQ ID NO: 5) 5'-GGTACATCTTGTTCA-3' (ARE). All other components were respectively the same. Copies of the ARE17 were introduced upstream from the TK minimal promoter and the luciferase gene in the pGL3-basic vector (FIG. 1). PC-3/AR cells, which already express the androgen receptor in a stable manner, were saturated in RPMI1640/10% cFS/L-glutamine for 18–24 hours and then transformed for five hours with 100 ng of reporter plasmid and the Fu-gene transfection reagent (Boehringer Mannheim). Then, the medium was replaced by RPM1640/5% cFCS/L-glutamine, and the activity of the reporter gene measured 42 hours later. A very strong induction of the luciferase activity in the presence of the androgen R1881 ($10^{-7}$ M) was measured (FIG. 2). The induction increased with the number of ARE17 copies in the reporter vector and was stronger than that which was observed with the consensus-HRE.

Figure 3:
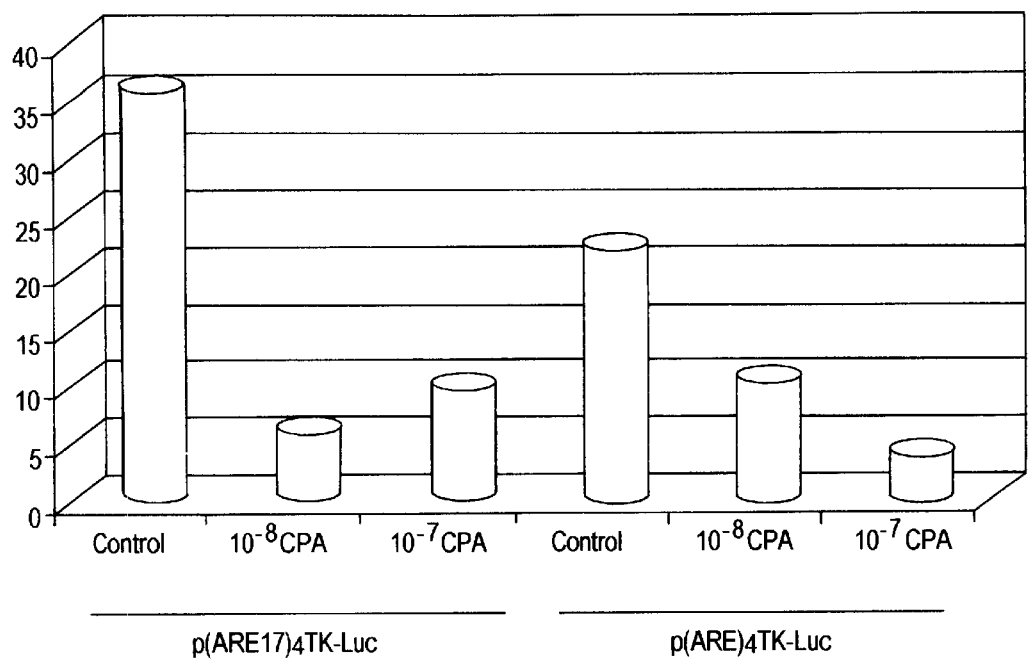
FIG. 3 shows the inhibition of the ARE17 according to the invention in comparison to a consensus-HRE (named ARE here) by an antiandrogen. Four copies of the element were introduced in the reporter vector. This was transformed in PC-3/AR cells, and the luciferase activity was measured after R1881 and cyproterone acetate treatment. The y-scale indicates how many times stronger the stimulation was in comparison to cells that were not treated with cyproterone acetate. The concentrations of the cyproterone acetate (CPA) are indicated in mol/l.

It was possible to inhibit the induction of ARE17 and of the consensus-HRE by the antiandrogen cyproterone acetate ($10^{-7}$M and $10^{-8}$M) (FIG. 3).

Figure 10:
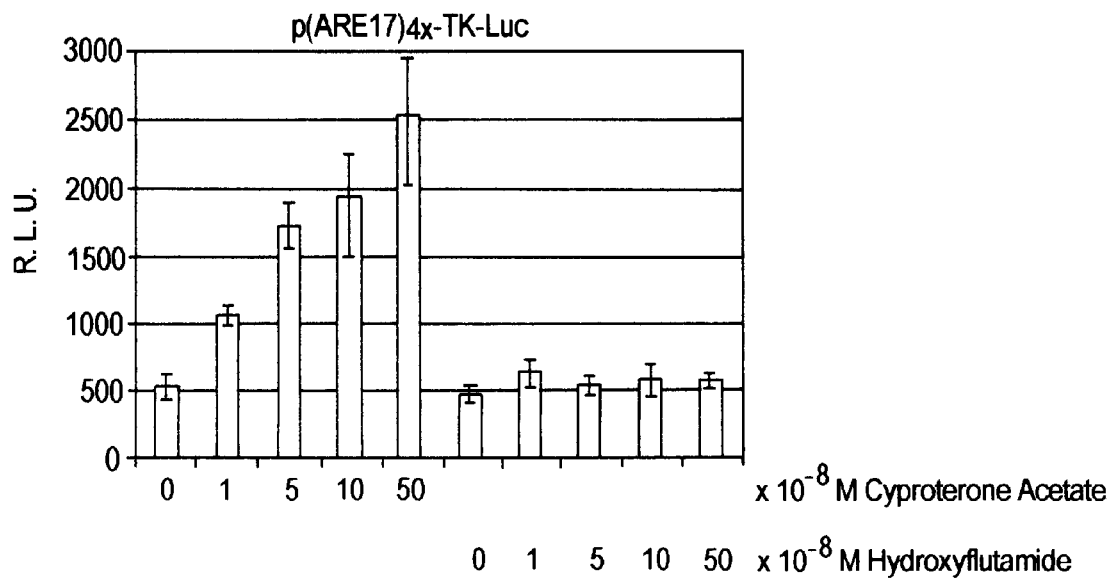
FIG. 10 shows the stimulation of the ARE17 according to the invention and the consensus-AREs by cyproterone acetate and hydroxyflutamide in the indicated concentrations. 4x refers to the number of copies of the element that was introduced into the reporter vector. The y-scale shows the luciferase activity in "relative light units (R.L.U.)."
Figure 10:
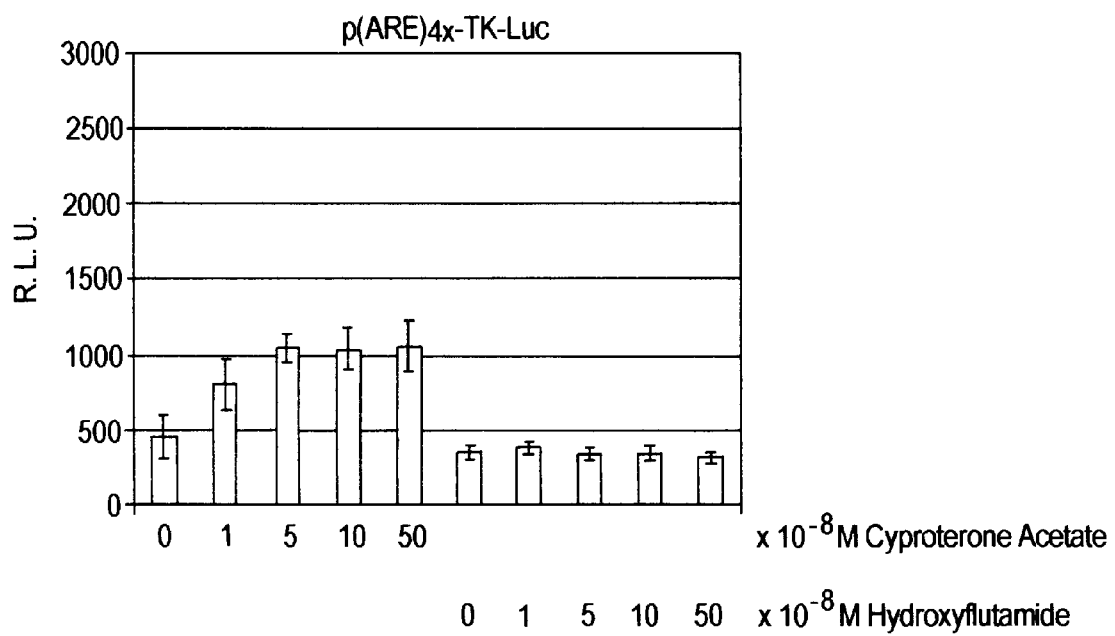

If these tests were performed in the absence of an androgen, cyproterone acetate showed a dose-dependent stimulation of ARE17 while it had only very little or no effect on the consensus-HRE (FIG. 10). The antiandrogen hydroxyflutamide stimulated neither ARE17 nor the consensus-HRE, however.

In further tests, the stimulation of the HRE according to the invention (ARE17), of the consensus-HRE with the sequence (SEQ ID NO: 5) 5'-GGTACATCTTGTTCA-3' or the IDR17-element with the sequence (SEQ ID NO: 9) 5'-GGAACGGAACATGTTCT-3' (Zhou et al. 1997, J. Biol. Chem. 272, 8227–8235) was compared. All other components were respectively the same.

Four copies of the elements were introduced upstream from the TK minimal promoter and the luciferase gene in the pGL3-basic vector (FIG. 1) and transformed in the PC-3/AR-cells, which already express the androgen receptor in a stable manner, as described above. The stimulation was carried out with the synthetic androgen R1881 ($10^{-9}$M or $10^{-7}$M final concentration). No decisive difference between the two quantities could be seen.

Figure 7:
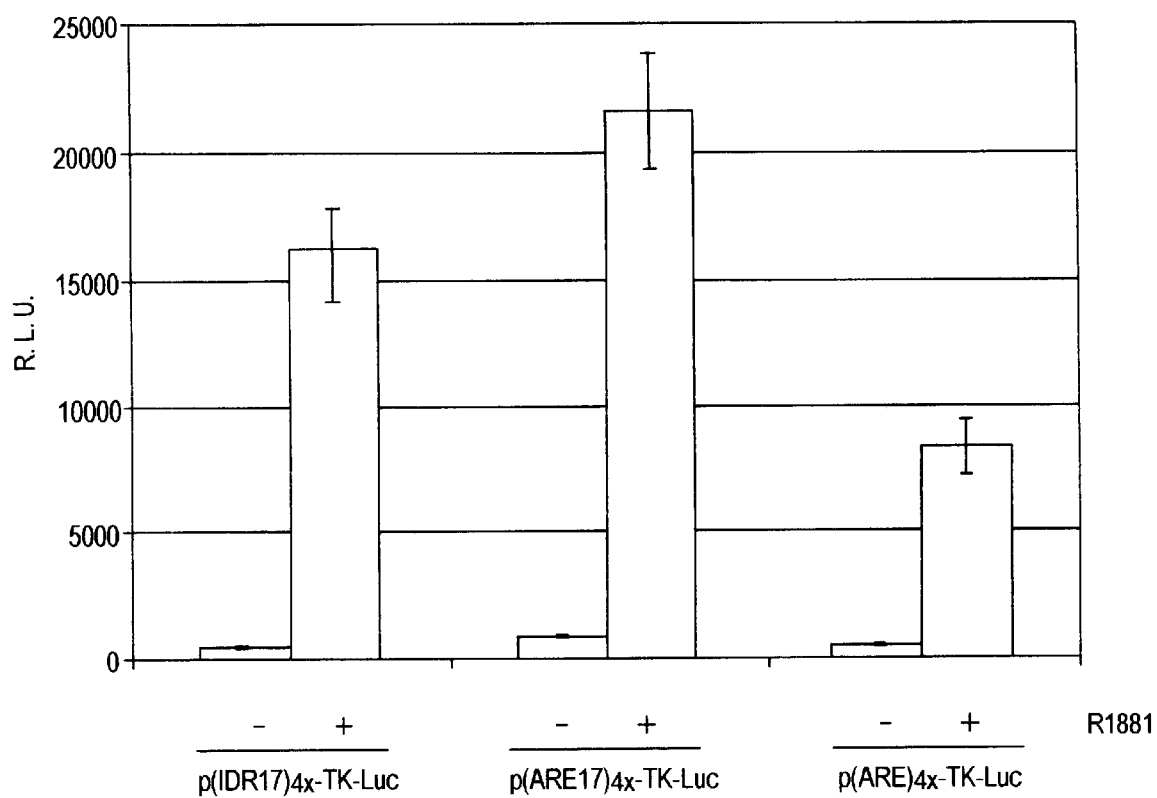
FIG. 7 shows the stimulation of the IDR17-HRE, of ARE17 according to the invention and of consensus-HRE (ARE) by the androgen R1881. 4x refers to the number of copies of the element that was introduced into the reporter vector. This was transformed in PC-3/AR cells, and the luciferase activity was measured after R1881 treatment. The y-scale shows the luciferase activity in "relative light units (R.L.U.)."

A comparison between the HRE according to the invention (ARE17), the consensus-HRE (ARE) and the IDR17-element showed the strongest induction of the luciferase activity in the presence of the androgen R1881 for the HRE according to the invention (ARE17) while the consensus-HRE (ARE) showed the weakest stimulation (FIG. 7).

Figure 8:
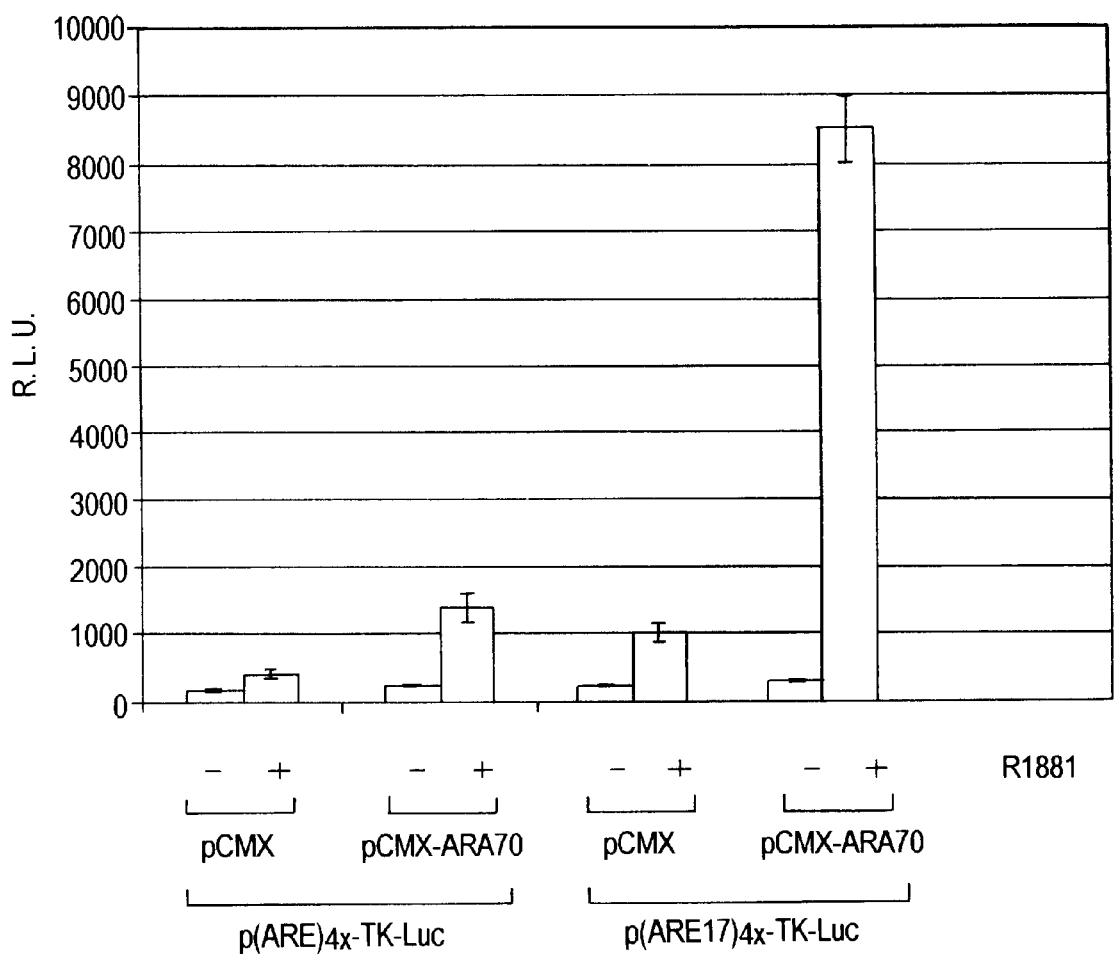
FIG. 8 shows the effect of cotransfection with the expression construct without (pCMX) and with the coactivator ARA70-insert (pCMX-ARA70) on the androgenic stimulation of the consensus-HRE (ARE) and of the ARE17 according to the invention. 4x refers to the number of copies of the element that was introduced into the reporter vector. The y-scale shows the luciferase activity in "relative light units (R.L.U.)."
Figure 9:
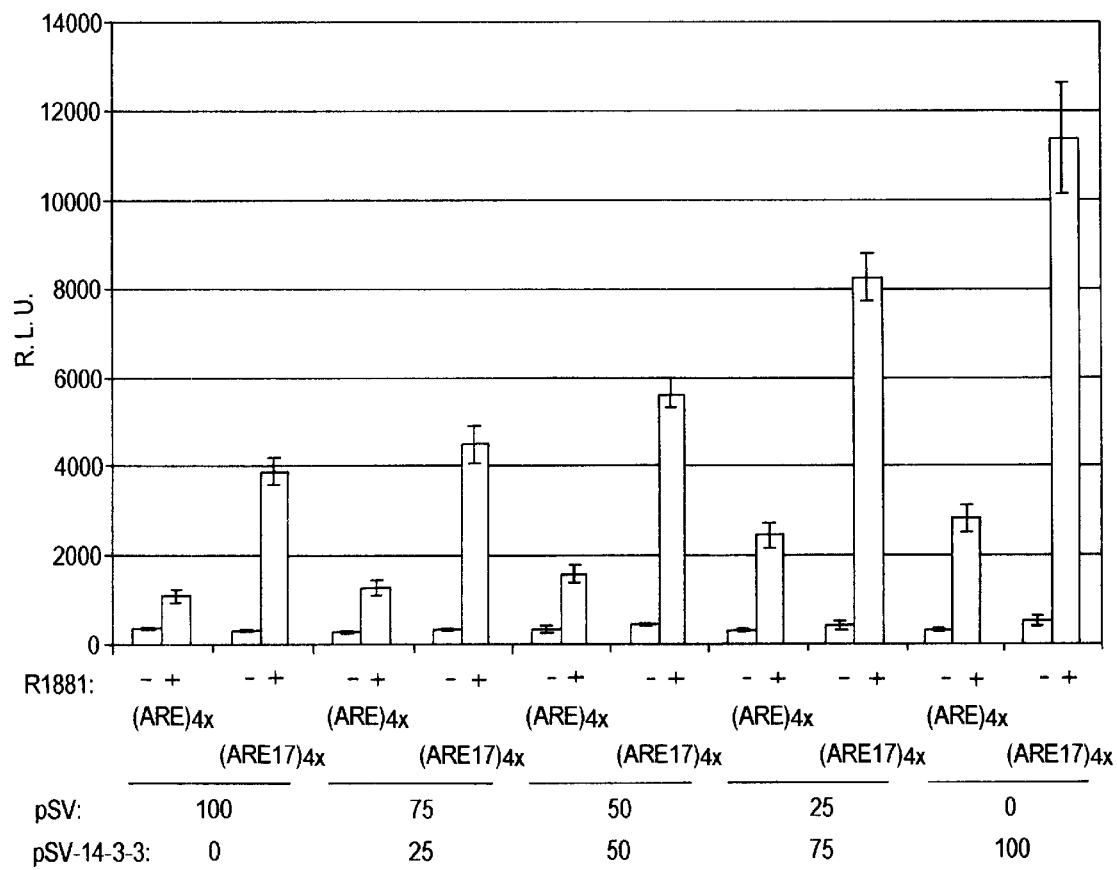
FIG. 9 shows the effect of cotransfection with the expression construct without (pSV) and with the 14-3-3η insert (pSV-14-3-3) on the androgen stimulation of the consensus-HRE (ARE) and the ARE17 according to the invention. 4x refers to the number of copies of the element that was introduced into the reporter vector. The quantities of pSV and pSV-14-3-3 in ng of plasmid that are transformed in each case are indicated. The total transformed amount of these two plasmids was kept constant at 100 ng. The y-scale shows the luciferase activity in "relative light units (R.L.U.)."

The additional transfection with the pCMX-ARA70 expression construct (100 ng), which codes for the androgen receptor-selective coactivator ARA70 (Yeh and Chang, 1996, Proc. Natl. Acad. Sci. 93, 5517–5521), showed a stimulation by R1881 compared to the control (100 ng of expression vector pCMX without insert), which was much more pronounced for the HRE according to the invention (ARE17) than for the consensus-HRE (ARE; FIG. 8). The cotransfection with the pSV-14-3-3η expression construct, which codes for the protein 14-3-3η (Muratake et al. 1995, Mol. Neurobiol. 11, 223–230), produced a dose-dependent stimulation of the androgen response, which was more pronounced for the HRE according to the invention (ARE17) than for the consensus-HRE (ARE; FIG. 9).

Figure 4:
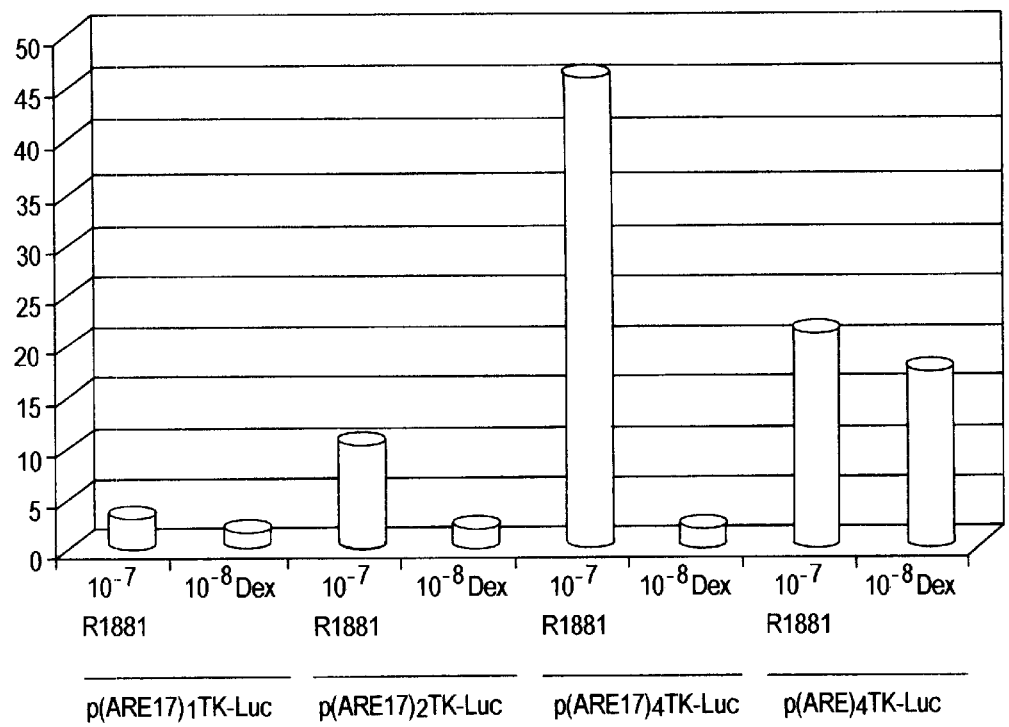
FIG. 4 shows the stimulation of the ARE17 according to the invention with an androgen or a glucocorticoid in comparison to a consensus-HRE (named ARE here). One to four copies of the elements were introduced into the reporter vector. This was transformed into PC-3/AR cells, and the luciferase activity after R1881- or dexamethasone treatment was measured. The y-scale indicates how many times stronger the stimulation was in comparison to cells that were not treated with androgen or glucocorticoid. The concentrations of R1881 and of dexamethasone (Dex) are indicated in mol/l.
Figure 5:
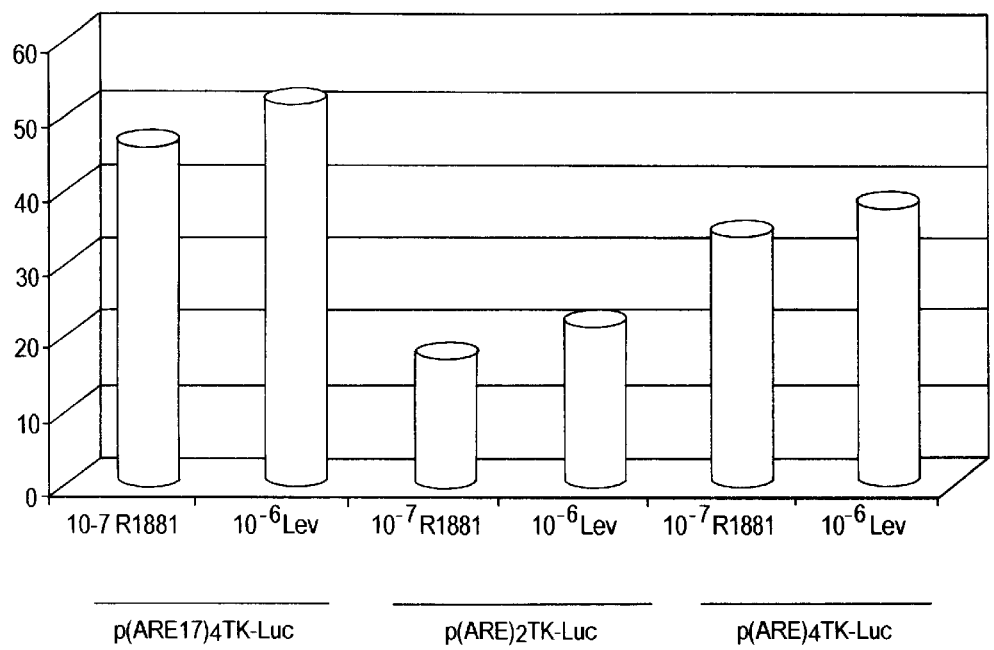
FIG. 5 shows the stimulation of the ARE17 according to the invention with an androgen or a progestin in comparison to a consensus-HRE. Two to four copies of the elements were introduced into the reporter vector. This was transformed in PC-3/AR cells, and the luciferase activity after R1881- or levonorgestrel treatment was measured. The y-scale indicates how many times stronger the stimulation was in comparison to cells that were not treated with androgen or progestin. The concentrations of R1881 and levonorgestrel (Lev) are indicated in mol/l.
Figure 6:
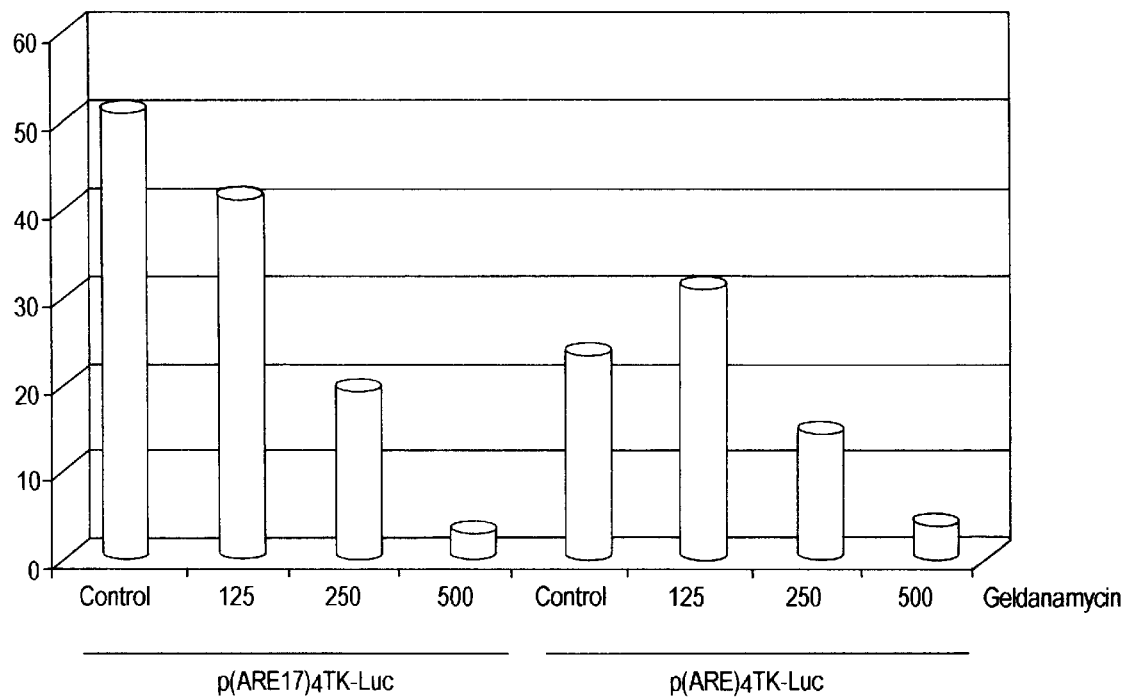
FIG. 6 shows the inhibition of the androgen stimulation of the ARE17 according to the invention by geldanamycin in comparison to a consensus-HRE. Four copies of the elements were introduced into the reporter vector. This was transformed in PC-3/AR cells, and the luciferase/activity was measured after R1881 and geldanamycin treatment. The geldanamycin concentration is indicated in ng/ml. In the control, no geldanamycin was used. The y-scale indicates how many times stronger the stimulation was in comparison to cells that were not treated with androgen.

A significant difference was seen when the ARE17 constructs and the consensus-HRE constructs were treated after cotransfection of the PC-3/AR cells with an expression vector for the glucocorticoid receptor with dexamethasone ($10^{-6}$ M). Here, virtually no stimulation for the ARE17 was seen, an effect that is comparable with the R1881 stimulation for the consensus-HRE (FIG. 4). In addition, it was noted that the ARE17 can be stimulated very greatly by the progestin levonorgestrel ($10^{-6}$ M) after cotransfection with an expression vector for the progesterone receptor (FIG. 5). Treatment by geldanamycin, a substance that inhibits the action of steroid receptors, showed that a low concentration (125 ng/ml) inhibits the androgen stimulation of the ARE17, but increases that of the consensus-HRE (FIG. 6).

The entire disclosure of all applications, patents and publications, cited above and below, and of corresponding German Application No. 198 55 013.8, filed Nov. 20, 1998 is hereby incorporated by reference.

What is claimed is:

1. An isolated non-protein-encoding nucleic acid sequence functioning as a hormone response element which binds an androgen- or a progesterone- regulated receptor, comprising:
   a DNA sequence of the formula (SEQ ID NO:6) (N)x TCTCATTCTGTTCC, wherein each N, independently of one another and in any combination, is A, T, C, or G, and X is equal to 0–3.

2. The non-protein-encoding nucleic acid sequence of claim 1, wherein x=0 and the DNA sequence corresponds to SEQ ID NO:3.

3. The non-protein-encoding nucleic acid sequence of claim 1, wherein X=3.

4. The non-protein-encoding nucleic acid sequence of claim 1, wherein N=AGA and the DNA sequence corresponds to SEQ ID NO: 1.

5. A vector that contains, in one or more copies, a non-protein encoding nucleic acid sequence according to claim 1, in operative linkage with a heterologous gene that is to be expressed.

6. The vector according to claim 5, wherein the operative linkage is the TK minimal promoter.

7. A cell transformed with a nucleic acid molecule according to claim 1 or with a vector according to claim 5.

8. The cell according to claim 7, which is a PC-3, a LNCaP, a CV-1, a HeLa or a Dunning cell.

9. A method of expressing a heterologous gene in a cell comprising transforming said cell with a vector according to claim 5.

10. The method of expressing a gene in a cell according to claim 9, wherein said cell contains a polypeptide which binds said hormone response element and said polypeptide has an androgen or progesterone binding site.

11. A method of expressing a protein comprising growing the cell of claim 7, in the presence of an androgen or a progesterone.

12. The method of expressing a protein in a cell according to claim 11, wherein said cell contains a polypeptide which binds the hormone response element and said polypeptide has an androgen or progesterone binding site.

13. A nucleic acid sequence consisting of the nucleic acid sequence of claim 1.

14. An isolated non-protein-encoding nucleic acid molecule functioning as a hormone response element which binds an androgen- or a progesterone regulated receptor, comprising:
   a DNA sequence of the formula (SEQ ID NO:6) (N)x TCTCATTCTGTTCC, wherein each N, independently of one another and in any combination, is A, T, C, or G, and X is equal to 0–3, wherein said nucleic acid molecule is in operative linkage with a heterologous gene.

15. A method of expressing a nucleic and sequence in a cell comprising transforming said cell with a vector which comprises a nucleic acid sequence that is operably linked with a hormone response element according to claim 1.

16. The method of expressing a nucleic acid sequence in a cell according to claim 15, wherein said cell contains a polypeptide which binds said hormone response element and said polypeptide has an androgen or progesterone binding site.

17. An isolated nucleic acid sequence functioning as a hormone response element which binds an androgen or a progesterone regulated receptor, comprising:

(a) a DNA sequence of the formula (SEQ ID NO:6) (N)x TCTCATTCTGTTCC, wherein each N, independently of one another and in any combination, is A, T, C, or G, and X is equal to 0–3; or (b) a DNA sequence, fully complementary to the DNA sequence of (a) with the proviso that said sequence is not operatively linked with Pem coding sequences.

18. The nucleic acid sequence of claim 17, wherein x=0 and the DNA sequence corresponds to SEQ ID NO:3.

19. The nucleic acid sequence of claim 17, wherein x=3.

20. The nucleic acid sequence of claim 17, wherein N=AGA and the DNA sequence corresponds to SEQ ID NO: 1.

21. A vector that contains, in one or more copies, a nucleic acid sequence according to claim 17, in operative linkage with a heterologous gene that is to be expressed.

22. A method of expressing a heterologous gene in a cell comprising transforming said cell with a vector according to claim 21.

23. The method of expressing a gene in a cell according to claim 22, wherein said cell contains a polypeptide which binds said hormone response element and said polypeptide has an androgen or progesterone binding site.

24. A method of expressing a protein comprising growing the cell of claim 23 in the presence of an androgen or a progesterone.

25. An isolated non-protein-encoding nucleic acid sequence functioning as a hormone response element which binds an androgen or a progesterone regulated receptor, comprising:

(a) a DNA sequence of the formula (SEQ ID NO:6)

(N)x TCTCATTCTGTTCC, wherein each N, independently of one another and in any combination, is A, T, C, or G, and X is equal to 0–3; or (b) a DNA sequence, fully complementary to the DNA sequence of (a)

wherein said nucleic acid molecule is in operative linkage with a heterologous gene.

26. A method of expressing a nucleic acid sequence in a cell comprising transforming said cell with a vector which comprises a nucleic acid sequence that is operably linked with a hormone response element according to claim 25.

27. The method of expressing a nucleic acid sequence in a cell according to claim 26, wherein said cell contains a polypeptide which binds said hormone response element and said polypeptide has an androgen or progesterone binding site.

28. A DNA sequence fully complementary to the DNA sequence of claim 1.

29. A DNA sequence fully complementary to the DNA sequence of claim 14.

* * * * *

SEQUENCE LISTING

```
<160> NUMBER OF SEQ ID NOS: 9

<210> SEQ ID NO 1
<211> LENGTH: 17
<212> TYPE: DNA
<213> ORGANISM: Rattus norvegicus

<400> SEQUENCE: 1
agatctcatt ctgttcc                                                    17

<210> SEQ ID NO 2
<211> LENGTH: 385
<212> TYPE: DNA
<213> ORGANISM: Mus musculus

<400> SEQUENCE: 2
tgagctgtaa ctgggcaccc taagttctgc acacccacat gcccatgaac tgtgtccatc    60
ttgcaagcac atcgtgctca ttacatcccc aaactgctat cacttgtgta ccccaaaggc   120
tcggcccaca ggaacgtcct gtgagcaaat cacaaagacc agcttagggc tggaaacatt   180
gtaacctgaa gtaggccaga ggagatccct gccaggttga gcatcacaga tctcattctg   240
ttcccgggga caccaggggc ccaagctcag aatctgccga agcataactt catcattgat   300
cctattcagg gtatggaagc tgagggttcc agccgcaagg tcaccaggct actccgcctg   360
ggagtcaagg aagactcgga agaac                                         385
```

```
<210> SEQ ID NO 3
<211> LENGTH: 14
<212> TYPE: DNA
<213> ORGANISM: Mus musculus

<400> SEQUENCE: 3
tctcattctg ttcc                                                          14

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (7)..(9)
<223> OTHER INFORMATION: "n" refers to any nucleotide

<400> SEQUENCE: 4
ggwacannnt gttct                                                         15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ggtacatctt gttca                                                         15

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: modified_base
<222> LOCATION: (1)..(3)
<223> OTHER INFORMATION: a region of 0-3 bases that may consist of a, t,
      c or g

<400> SEQUENCE: 6
nnntctcatt ctgttcc                                                       17

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
gttcttccga gtcttccttg ac                                                 22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
gtaatacgac tcactatagg gc                                                 22
```

-continued

```
<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
ggaacggaac atgttct                                                      17
```